US00PP09094P

United States Patent [19]

Fuess

[11] Patent Number: Plant 9,094

[45] Date of Patent: Mar. 28, 1995

[54] CHRYSANTHEMUM PLANT NAMED EMPIRE CITRINE

[76] Inventor: Janet S. Fuess, 22 Country Club Dr., New York Mills, N.Y. 13417-1456

[21] Appl. No.: 281,109

[22] Filed: Jul. 28, 1994

[51] Int. Cl.[6] ..... A01H 5/00

[52] U.S. Cl. ..... Plt./82.2

[58] Field of Search ..... Plt. 82.2

[56] References Cited

U.S. PATENT DOCUMENTS

P.P. 5,989 5/1987 Duffett et al. ..... Plt./82.2

P.P. 6,774 5/1989 VandenBerg ..... Plt./82.2

*Primary Examiner*—Howard J. Locker

*Attorney, Agent, or Firm*—Foley & Lardner

[57] ABSTRACT

A Chrysanthemum plant named Empire Citrine, particularly characterized by its flat capitulum form; daisy capitulum type with 2 to 3 rows of ray florets; light yellow ray floret color; flowers have an average of 57 ray florets and 161 disc florets; diameter across face of capitulum of 45 to 50 mm when fully open; fully expanded ray florets approximately 23 mm long and 7 mm wide with dentate tips; ray florets open with a spoon shape and as they mature, remain closed at base and broaden to a wide flat keel, tapering to a rounded dentate tip; early natural season flowering date of September 15 in Hartford, N.Y.; flowering response of 7.5 weeks in a controlled Light/Shade program; compact growth habit with good spread and breaking, exhibiting 8 to 10 branches per plant after pinch two weeks after planting rooted cutting in New Hartford, N.Y.; compact cushion habit makes it suitable for production in 4" to 8" containers; and adaptability to greenhouse or garden cultures.

3 Drawing Sheets

1

The present invention comprises a new and distinct cultivar of Chrysanthemum, botanically known as *Dendranthema grandiflora,* and referred to by the cultivar name Empire Citrine.

Empire Citrine is a product of a planned breeding program which had the objective of creating new Chrysanthemum cultivars with freely branching and compact cushion habits, early flowering response, and daisy flowers with many ray florets, making it suitable for production as a garden variety. Such traits in combination were not present or needed improvement in previously available commercial cultivars.

Empire Citrine was originated from a hybridization by Janet S. Fuess in a controlled breeding program in New Hartford, N.Y. in October 1988.

The female parent of Empire Citrine was an unnamed seedling identified as F87-6, and described as a golden yellow decorative garden mum.

The male parent of Empire Citrine was the cultivar identified as White Stardom, disclosed in U.S. Plant Pat. No. 3,999, and described as a white duplex daisy garden mum.

Empire Citrine was discovered and selected as one flowering plant within the progeny of the started cross by Janet S. Fuess in August 1989 in a controlled environment in New Hartford, N.Y.

The first act of asexual reproduction of Empire Citrine was accomplished when vegetative cuttings were taken from the initial selection in October 1989 in a controlled environment in New Hartford, N.Y. by a technician working under formulations established and supervised by Janet S. Fuess.

Horticultural examination of selected units initiated in August 1990 has demonstrated that the unique combination of characteristics as herein disclosed for Empire Citrine are firmly fixed and are retained through successive generations of asexual reproduction.

Empire Citrine has not been observed under all possible environmental conditions. The phenotype may vary significantly with variations in environment such as temperature, light intensity, and daylength, without, however, any variance in genotype.

2

The following observations, measurements and comparisons describe plants grown in New Hartford, N.Y. under outside natural season conditions which approximate those generally used in commercial practice.

The following traits have been repeatedly observed and are determined to be basic characteristics of Empire Citrine, which, in combination, distinguish this Chrysanthemum as a new and distinct cultivar:

1. Flat capitulum form.
2. Daisy capitulum type with 2 to 3 rows of ray florets.
3. Light yellow floret color.
4. Flowers have an average of 57 ray florets and 161 disc florets.
5. Diameter across face of capitulum of 45 to 50 mm when fully open.
6. Fully expanded ray florets are approximately 23 mm long and 7 mm wide with dentate tips.
7. Ray florets open with a spoon shape. As they mature, they remain closed at base and broaden to a wide flat keel, tapering to a rounded dentate tip.
8. Early natural season flowering date of September 15 in New Hartford, N.Y.
9. In a controlled Light/Shade Program, the new cultivar has a flowering response of 7.5 weeks.
10. Compact growth habit, with good spread and branching. There are 8 to 10 branches per plant after pinch two weeks after planting a rooted cutting in New Hartford, N.Y.
11. Compact cushion habit makes it suitable for production in 4" to 8" containers.
12. Adaptability to greenhouse or garden cultures.

The accompanying photographic drawings show typical inflorescence and leaf characteristics of Empire Citrine, with the colors being as nearly true as possible with illustrations of this type.

Sheet 1 is a color photograph of Empire Citrine grown under greenhouse conditions in Ft. Myers, Fla.

Sheet 2 is a black and white photograph of three views of the inflorescence of Empire Citrine.

Sheet 3 is a black and white photograph showing the upper and under sides of the leaves of Empire Citrine at three stages of development (mature, intermediate, and immature). In sheets 2 and 3 a measuring tape in centimeters has been added.

Of the commercial cultivars known to the inventor, the most similar in comparison to Empire Citrine is the cultivar Donna, disclosed in U.S. Plant Pat. No. 7,412. Reference is made to Chart A, which compares certain characteristics of Empire Citrine to the same characteristics of Donna.

Similar traits are flat capitulum form, plant height and branching pattern. Empire Citrine has, when compared to Donna, an earlier natural season response time, slightly longer controlled flowering response, time, smaller diameter of capitulum, a flat, mature ray floret shape, and lighter yellow ray floret color.

In the following description, color references are made to the Royal Horticulture Society Colour Chart. The color values are based on plant material grown in a controlled greenhouse in Ft. Myers, Fla., and were determined on Jun. 8, 1994 between the hours of 10:00 a.m. and 1:00 p.m. in an office by a south window under cool white fluorescent lighting.

Classification:

*Botanical.*—Dendranthema grandiflora cv Empire Citrine.

*Commercial.*—Flat daisy garden mum.

INFLORESCENCE

A. Capitulum:

*Form.*—Flat.

*Type.*—Daisy with 2 to 3 rows of ray florets.

*Diameter across face.*—45 to 50 mm when fully open.

B. Corolla of ray florets:

*Color (general tonality from a distance of three meters).*—Light yellow.

*Color (upper surface).*—Young flowers at 25% open 6B, fading to 6D upon flower maturity. General tonality 11B.

*Color (under surface):*—8C.

*Shape.*—Opens as spoon. As ray floret Matures, it remains closed at base, but broadens to a wide flat keel tapering to a dentate tip.

C. Corolla of disc florets:

*Color (mature).*—Most closely resembles 14A.

*Color (immature).*—Most closely resembles 154D.

D. Reproductive organs:

*Androecium.*—Present on disc florets only; moderate pollen.

*Gynoecium.*—Present on both ray and disc florets.

PLANT

A. General appearance:

*Height.*—24 to 28 cm when grown in fall under natural daylength in New York with no growth regulators.

*Branching pattern.*—Spreading and prolific. There are 8 to 10 branches per plant after pinch two weeks after planting a rooted cutting in New Hartford.

B. Foliage:

*Color (upper surface).*—147A.

*Color (under surface).*—Between 147A and 147B.

*Shape.*—See photograph.

CHART A

| CULTIVAR | EMPIRE CITRINE | DONNA |
|---|---|---|
| Ray floret color | Light Yellow | Yellow |
| Capitulum form and type | Flat Daisy | Flat Spooned Daisy |
| Diameter across face of capitulum | 45–50 mm | 63–75 mm |
| Branching pattern | Spreading and prolific | Spreading and prolific |
| Controlled response | 7.5 Weeks | 7.0 Weeks |
| Average natural season flower date in New Hartford, NY and Hightstown, NJ | September 15 | September 27 |

COMPARISONS MADE OF PLANTS GROWN AS UNDER NATURAL SEASON OUTDOOR CONDITIONS IN NEW HARTFORD, NY AND HIGHTSTOWN, NJ

I claim:

1. A new and distinct Chrysanthemum plant named Empire Citrine, as described and illustrated.

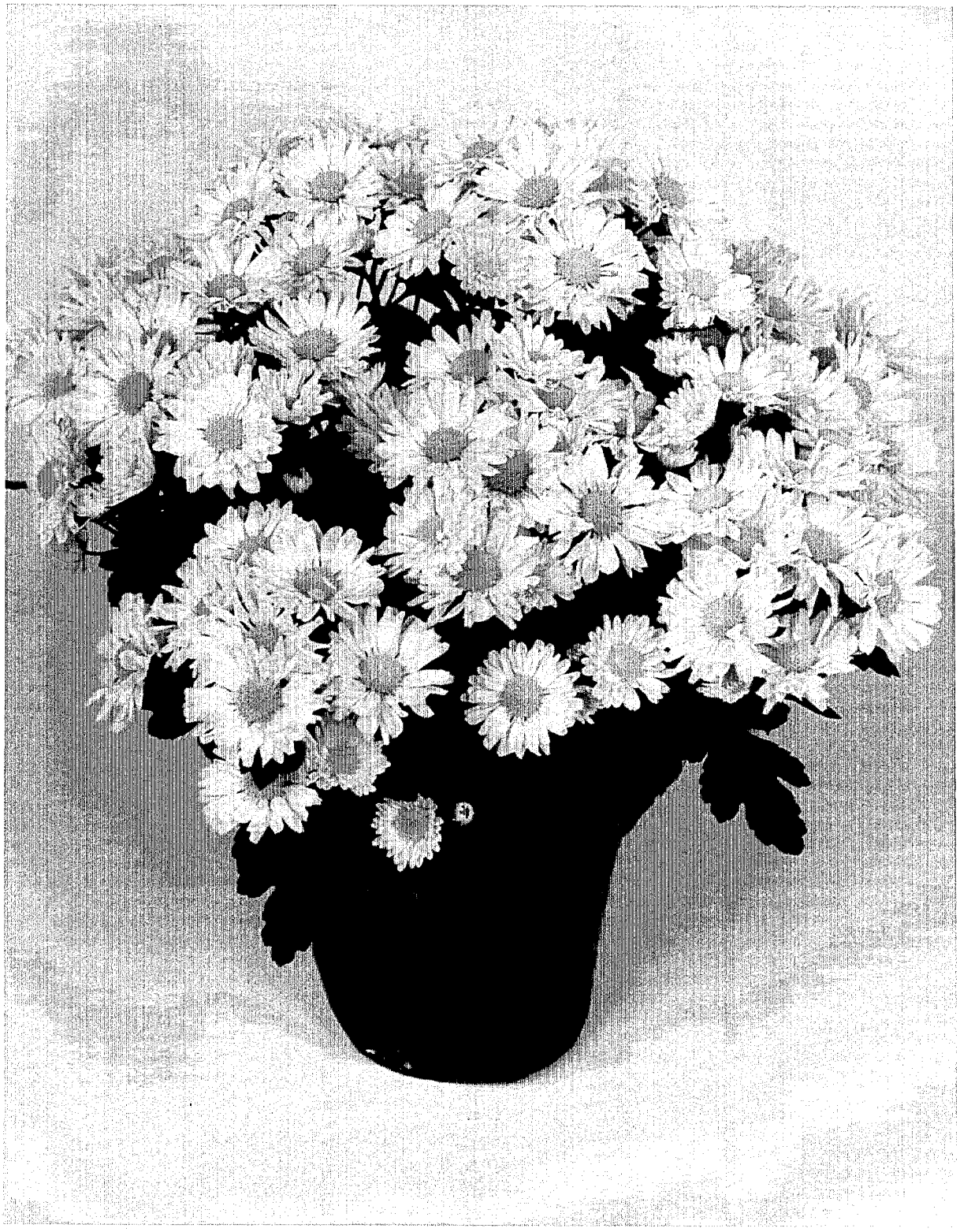

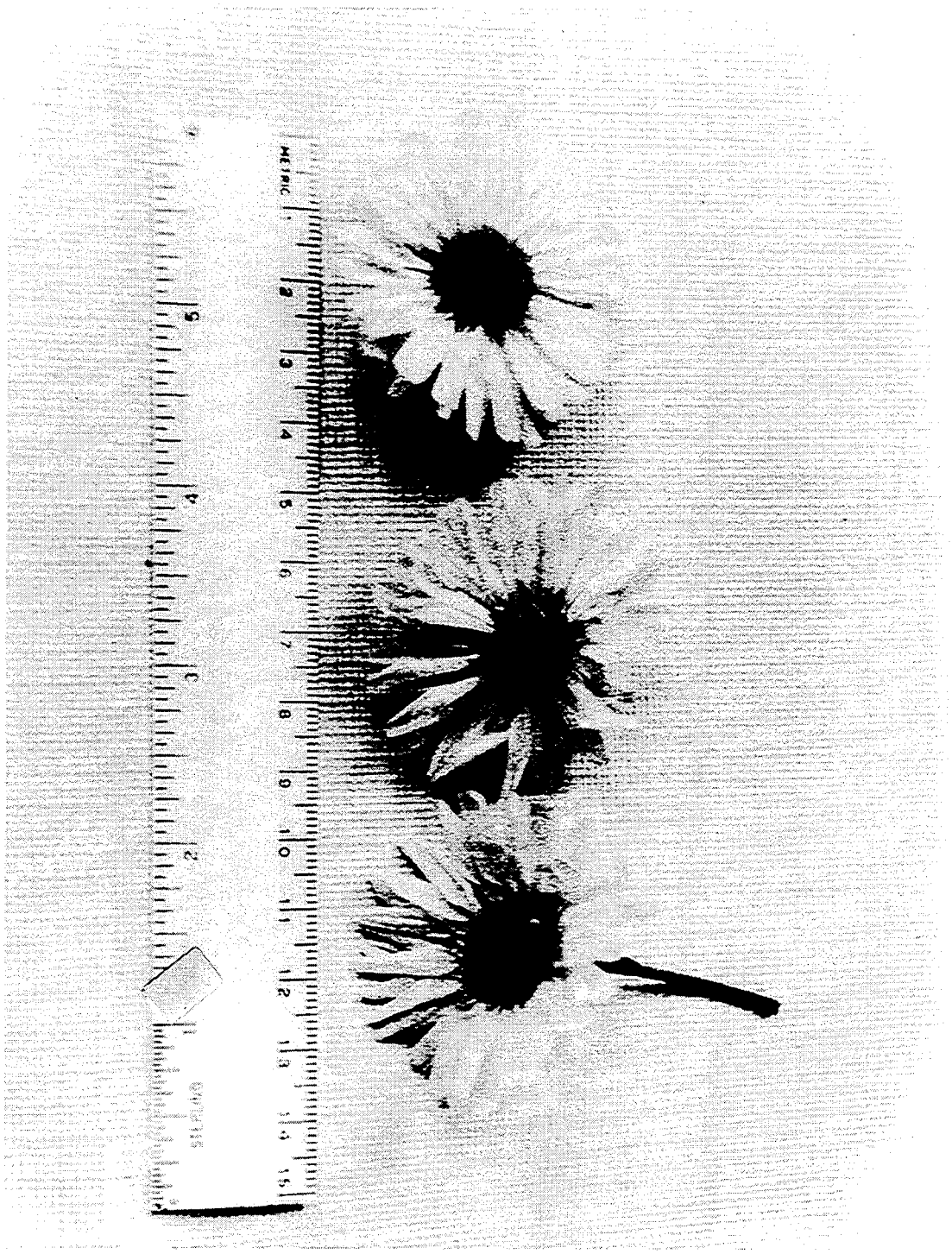

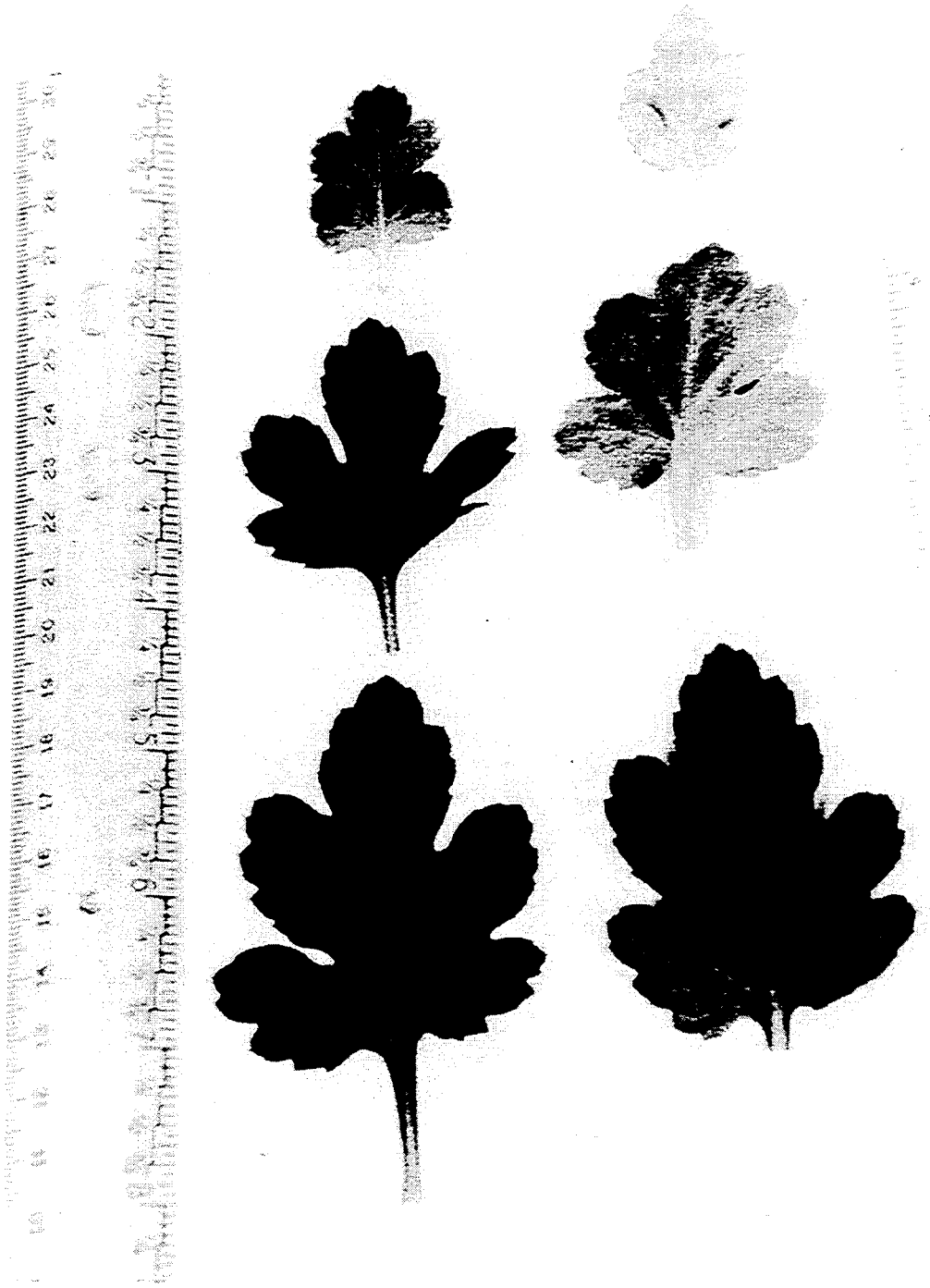

* * * * *